United States Patent [19]

Roy

[11] Patent Number: 4,826,679
[45] Date of Patent: May 2, 1989

[54] COMPOSITION AND METHODS FOR ALLEVIATING CYSTIC FIBROSIS

[75] Inventor: Claude C. Roy, Quebec, Canada

[73] Assignee: Universite de Montreal, Montreal, Canada

[21] Appl. No.: 866,347

[22] Filed: May 23, 1986

[51] Int. Cl.⁴ .................... A61K 31/195; A61K 37/48
[52] U.S. Cl. ................................. 424/94.21; 514/562; 514/851
[58] Field of Search ....................... 514/578, 562, 851; 424/94

[56] References Cited

U.S. PATENT DOCUMENTS

| 3,728,444 | 4/1973 | Cook | 424/315 |
|---|---|---|---|
| 3,899,589 | 8/1975 | Cook | 424/315 |
| 3,920,833 | 11/1973 | Cook | 424/303 |
| 4,545,977 | 10/1985 | Gaull | 424/10 |

FOREIGN PATENT DOCUMENTS

| 2329753 | 12/1973 | Fed. Rep. of Germany . |
|---|---|---|
| 2443431 | 3/1975 | Fed. Rep. of Germany . |
| 102822 | 9/1974 | Japan . |
| 62558 | 8/1975 | Japan . |
| 58-156211 | 12/1981 | Japan . |
| 58-27559 | 2/1983 | Japan . |
| 58-103355 | 6/1983 | Japan . |
| 58-140017 | 8/1983 | Japan . |
| 58-208212 | 12/1983 | Japan . |
| 735273 | 10/1974 | Netherlands . |

OTHER PUBLICATIONS

Pediatric Research, 1985, vol. 19, pp. 578-582, Darling et al.
Chemical Abstracts, 89:70974g, (1978).
Chemical Abstracts, 94:96860v, (1981).

*Primary Examiner*—Leonard Schenkman
*Attorney, Agent, or Firm*—Cushman, Darby & Cushman

[57] ABSTRACT

The invention relates to an oral composition for alleviating digestive manifestations in patients afflicted with cystic fibrosis, which comprises a therapeutic amount of taurine in association with a pharmaceutically acceptable carrier, and to a method of alleviating digestive manifestations in patients afflicted with cystic fibrosis by the administration of said oral composition.

4 Claims, No Drawings

COMPOSITION AND METHODS FOR ALLEVIATING CYSTIC FIBROSIS

BACKGROUND OF THE INVENTION

Cystic fibrosis is an inherited disease of the exocrine glands and exocrine sweat glands which primarily affects the digestive and respiratory systems. This disease usually characterized by chronic respiratory infections, pancreatic insufficiency, abnormally viscid mucuous secretions and premature death.

The main clinical effects of cystic fibrosis are observed in evidence of respiratory tract involvement and pancreatic insufficiency characterized by failure to grow despite an excellent appetite, frequent foul stools and abnormal pancreatic function tests.

As far as the respiratory tract is concerned life expectancy can be improved by preventing pulmonary complications or by treating them early. Treatment includes preventing airway obstruction, as well as controlling infection. Many ways of treating pulmonary complications in patients having cystic fibrosis are known to the medical profession specializing in the treatment of this disease.

Pancreatic insufficiency is normally treated with pancreatic enzyme replacement in the form of powder, tablets or capsules which are given before each meal with the dosage varying with the size of the meal, the potency of the preparation and the stool pattern. As an example of a product used for pancreatic enzyme replacement there may be mentioned pancrelipase sold under the trade mark PANCREASE® by McNeil Pharmaceutical (Canada) Ltd. This product contains lipase, amylase and protease enzymes.

Nutritional support has become a priority since life expectancy appears to be improved when attention is paid to nutrition and growth. There are also products which provide high protein intake along with multivitamins and trace elements which are also incorporated in the diet.

Current recommendations include a normal intake of fat essential to insure adequate nutrition and integrity of membranes. However it is known that despite the presence of pancreatic enzymes absorption of fat is decreased.

Since fat absorption is an important factor in the treatment of cystic fibrosis it would appear highly desirable if a product could be found which, when taken alone or with a dietary supplement, would favor an improved fat absorption.

SUMMARY OF THE INVENTION

In accordance with the present invention, it has now been found that taurine either alone or in association with a diet therapy is surprisingly useful in enhancing fat absorption in individuals suffering from cystic fibrosis.

More specifically, it has been found that the daily administration of about 30 mg/kg of body weight of taurine in association with a pharmaceutically acceptable carrier enhances the absorption of fat and is associated with a documented increase in weight accompanied by a more modest increase in height of patients given taurine supplements over a six month period.

More specifically, it has been found, in accordance with the present invention that the daily administration of about 30 mg/kg of body weight of taurine in association with a pharmaceutically acceptable carrier alleviates the digestive manifestations of cystic fibrosis. The novel composition of the present invention has been shown to be useful to alleviate digestive manifestations and to improve growth; there is also evidence that it could also be useful to prevent and treat biliary complications.

DETAILED DESCRIPTION OF THE INVENTION

More specifically, it has been found that patients with cystic fibrosis have an increased proportion of glycine conjugated bile acids with diminished tauroconjugates which could thus contribute to fat malabsorption. Taurine normally found in bile conjugated with bile acids is found in smaller amount in the bile of patients with cystic fibrosis. The daily administration of about 30 mg/kg of body weight surprisingly increased the tauroconjugates in bile acids thus favoring the absorption of fat because of their ability to remain in solution at the acid pH of the duodenum of cystic fibrosis patients.

The novel composition of the present invention is preferably administered in the form of capsules or tablets and comprises a mixture of taurine in admixture with the usual excipient normally used in association with the administration of oral dosage forms. Taurine could also be associated with other products used in the treatment of cystic fibrosis, for example, with pancrelipase.

The daily dosage administered to cystic fibrosis patient is about 30 mg/kg of body weight and may be administered daily in a single dosage unit or in several dosage units depending on each case. The essential thing is that the total daily intake of taurine by a patient is about 30 mg/kg of body weight.

It is a feature of the present invention that the daily administration of a taurine supplement will decrease the glycine/taurine ratio thereby favoring fat absorption in cystic fibrosis patients.

After controlled clinical trials on young patients suffering from cystic fibrosis it was found that the ratio of glycine/taurine conjugated bile acids was decreased. It was also found that there was a decrease in steatorrhea $17.6 \pm 9.7\%$ while the patients were on a taurine supplement. It was further found that taurine has a particularly evident effect for long-chain saturated fatty acids which were consistently reduced except for the C14:0. Linolenic acid was decreased two-fold but little change in linoleic acid was noted.

In many patients presenting steatorrhea, a greater loss of fatty acids was observed for the ones on a taurine supplement than for those patients on a placebo. It was also noted that some patients showed an increased weight velocity while others showed an improvement in height velocity over a 6-month treatment period with taurine.

The present invention will be more fully understood by referring to the following clinical trials and the results obtained.

Patients and Methods

Twenty-two CF (cystic fibrosis) children, 14 boys and eight girls, with a mean age of 7 5/12 yr (2–16 yr) were admitted to the study on documentation of steatorrhea off pancreatic enzymes (>5 g/24 h). Two patients had hepatomegaly but no echographic evidence of cirrhosis. Bilirubin and aspartate aminotransferase levels were normal; however, seven patients had either a fasting or a 90-min postprandial level of cholylglycine (Radioimmunoassay diagnostic kit, Abbott Laboratories, Ltd., Montreal, Quebec) above 100 μg/dl. The average height as percentage of expected height for age was 97.1 (88.4–105.4) while weight as percentage of expected weight for height averaged 101.0 (86.5–123.6). The Shwachman score (Am. J. Dis Child 96:6–15) ranged from 64–98 with a mean of 84.

Patients were randomly assigned to receive either taurine 30 mg/kg/day capsules or placebo (lactose) during an initial 6-month period after which each patient received the alternate supplement during a second 6-month period. The study was carried out on an ambulatory basis and the children continued to consume their usual diet containing 40–45% fat. With regard to pancreatic enzyme therapy, the type (Pancrease ®) and number of capsules taken remained the same during the study except in three patients in whom a change from Cotazyme ® to Pancrease ® was made. In two of these patients, the switch to Pancrease ® occurred while they were on placebo. Vitamin supplementation and physiotherapy were maintained. Oral cloxacillin was continued for the entire duration of the study in 13 patients. Cloxacillin was used intermittently in the others.

Seventy-two hour stool collections were obtained between carmine red markers at the end of each 6-month period. Stools were frozen on evacuation and kept in the home freezer until the scheduled clinic appointments. On delivery to the laboratory feces were weighed, diluted with water (1:1, v/v), and homogenized. The stool homogenates were diluted with ethanol 90% (1:1, v/v) in order to prevent further degradation of bile acids. The homogenates were then kept at −20° C. until subsequent analysis for fatty acids, bile acids, neutral sterols, and nitrogen.

Fecal Fat

Fecal fat was quantitated by a recently described technique (J. Lipid Res 25:1391–1396). This method consists of the analysis of total fatty acids by gas-liquid chromatography. Unlike currently used methods which require numerous preparative steps, this technique involves a one-step reaction which is carried out in the same tube, thereby leading to a more complete recovery of fatty acid constituents of all classes of lipids. Briefly, the stool homogenate, from which ethanol was removed under nitrogen, was added with an internal standard consisting of tridecanoic acid dissolved in methanol:benzene, 3:2 (v/v). Direct transesterification was then carried out by adding 1 ml of acetyl chloride:methanol, 5:100 (v/v) to the stool and internal standard mixture. The closed tube was then heated at 100° C. for 1 h. Following the reaction, 1 ml of an external standard solution, consisting of 500 μg of methylated pentadecanoic acid dissolved in hexane, was added to the reaction mixture along with 1 ml of distilled water. After centrifugation, an aliquot of the upper phase containing the methyl esters was injected into the gas chromatograph, a Hewlett-Packard 5880 equipped with a flame ionization detector. A 10-ft glass column with an internal diameter of 2 mm and packed with 5% SP-2340 on chromosorb W-AW (100–120 mesh) was used. Individual fatty acids were determined based on known quantities of the internal standard.

Fecal Bile Acids, Neutral Sterols, and Nitrogen

Fecal bile acids and neutral sterols were measured from the aqueous ethanolic fecal homogenates of patients who excreted more than 10 g of fatty acids per day on placebo. Each determination was carried out in duplicate and the coefficient of variation did not exceed 10%. After weighing, the internal standard, 23-nordeoxycholic acid, was added to the homogenate. Following alkaline hydrolysis and acidification, free bile acids were extracted and thin layer chromatography was used to remove remnant lipids. Derivatization of bile acids was performed using a solution of acetyl chloride-methanol, followed by heating. Total and individual bile acids were quantitated with a Hewlett-Packard 5880 gas chromatograph using a 6-foot column packed with 2% QF1 on chromasorb W (HP) 100:120 mesh. Samples for neutral sterol determination were added with the internal standard 5α-cholestane. The mixture was refluxed with NaOH-ethanol for one hour and then extracted with petroleum ether. The same column as for bile acids was used for gas liquid chromatography of neutral sterols. Fecal nitrogen was determined in duplicate by a modified Kjeldahl procedure (Pediatric Microbiochemical Techniques, Harper and Row Publishers, New York, pp 238–240).

Blood was collected after an overnight fast in Vacutainer tubes containing EDTA. Plasma was rapidly separated and stored at −20° C. until analysis of fatty acids using the same technique as the one summarized above for fecal homogenates. Cholesterol was measured with the modified Liebermann-Burchard reagent and was determined simultaneously with triglycerides using a Technicon autoanalyzer. Bile samples were obtained in two patients while on placebo and on taurine through a weighted polyethylene tube positioned in the second portion of the duodenum following the iv injection of cholecystokynin-pancreozymin (1.5 U/kg).

At the end of each treatment period, a questionnaire was addressed to the parents prior to clinic visits during which answers were verified. Particular attention was paid to appetite, frequency and consistency of stools, abdominal pain, and bloating. During trimonthly clinic visits anthropometric measurements were made. Height and weight velocities during the placebo and taurine treatment periods were compared to the standards of Tanner et al. (Arch Dis Child 41:613–625) and expressed as a percentage of expected velocities for age during each 6-month period.

All results are expressed as $\bar{X}\pm SE$. Response to taurine was evaluated using paired and unpaired Student's/tests as described for the analysis of cross-over clinical trial (Br. J. Pharmacol 8:7–20). Testing for linearity of regression between percentage decrease of individual fatty acids and their respective log solubility values was done using analysis of variance technique.

RESULTS

Of the 22 original patients, three dropped out of the study because of lack of compliance. Appetite and gastrointestinal manifestations did not change. However, constipation was noted in one patient on 1.4 g of taurine which was then decreased to 0.9 g. During the two treatment periods, four patients had to be admitted to hospital for exacerbations of pulmonary disease requiring iv antibiotic therapy while receiving placebo and three during the treatment period with taurine. The Shwachman scores of the 19 patients completing the 1-yr study did not change. In response to taurine, the ratio of G/T conjugated bile acids changed from 7.05 to 1.19 in the two patients in whom bile was obtained during both periods of the study.

Most patients (14/19) showed a decrease of steatorrhea which overall was reduced by $17.6 \pm 9.7\%$ while on taurine. This significant ($p < 0.05$) effect of taurine was particularly evident for long-chain saturated fatty acids. They were consistently reduced except for C14:0 (Table 1). Linolenic acid (C18:3) was decreased two-fold but there was little change in linoleic acid (C18:2). Taurine was somewhat more beneficial in the 10 patients with a greater degree of steatorrhea ($>10$ g/day). In that group, the percentage decrease of fat loss approached 20% and a close relationship was observed ($r=0.84$, $p<0.01$) between fatty acid loss on placebo and the improvement observed while on taurine. The percentage decrease of individual fatty acids accounting for 75% of total fat was plotted against their respective values for log solubility in water. A linear relationship was found between both variables since the percentage reduction of fatty acid loss increased as their individual aqueous solubility decreased.

In contrast to fatty acids, neither the excretion of neutral sterols nor of acidic sterols (bile acids) was changed by the administration of taurine. In the majority of patients (7/10), neutral sterols consisted only of cholesterol as coprostanol and coprostanone were totally absent. Little change was noted in total bile acid excretion. The percentage of primary bile acids (cholic and chenodeoxycholic acid) during the placebo period was $54.7 \pm 7.7$ and $53.1 \pm 9.4\%$ on taurine. The ratio of these two primary bile acids added with their respective degradation products which are formed by the intestinal flora was the same on placebo ($1.50 \pm 0.15$) as on taurine ($1.67 \pm 0.15$).

Nitrogen excretion during the placebo period was $1.78 \pm 0.18$ g/24 h and did not differ from the figure of $2.01 \pm 0.32$ g/24 h documented while the subjects were on taurine which contributed only 3.4 mg/kg/day to their daily nitrogen intake.

The total plasma fatty acids (mg/dl) and individual fatty acids, expressed as a percentage of the total, did not differ in the 10 patients who had the most significant degree of steatorrhea. All had detectable amounts of 5, 8, 11 eicosatrienoic acid (C20:3 $\omega$9). Concentrations on taurine ($0.46 \pm 0.04$) were the same as on placebo ($0.48 \pm 0.10$). The ratio of C20:3 $\omega$9 over C20:4 $\omega$6 (arachidonic acid) showed no change: it was $0.086 \pm 0.013$ on taurine and $0.088 \pm 0.016$ on placebo. Fasting cholesterol and triglyceride levels (mg/dl) were the same on taurine ($118 \pm 4$ and $99.4 \pm 20.7$) as on placebo ($113 \pm 4$ and $78.7 \pm 9.4$).

Of 18 patients in whom growth data were obtained, 11 showed an increased weight velocity while only eight showed an improvement in height velocity during the 6-month treatment period with taurine. The average ($\bar{X} \pm SE$) weight increase, expressed as a percentage of the predicted increase for age, was $117.1 \pm 16.5$ on taurine compared to $83.4 \pm 11.3$ on placebo for the entire group. However, the difference was of borderline significance as the p value was $<0.1$. Although children on taurine had an average percentage increase of linear growth to $110.7 \pm 10.6$ which was greater than the corresponding figure of $95.3 \pm 7.8$ obtained while they were on placebo there was a wide overlap. Further analysis of the data showed that there was no carry over effect of taurine which could have interfered with the growth response to treatment.

DISCUSSION

This study has shown that a taurine supplement of 30 mg/kg/day administered over 6 months in a two-period single blind cross-over trial had a beneficial effect on fat malabsorption and produced a marginally significant increase in weight velocity.

Taurine supplementation in healthy adults led to a reversal of the G/T conjugation ratio or at least to a decrease in the G/T ratio of conjugated bile acids. However, neither of these studies addressed the issue of the physiological implications of shifting the conjugation pattern on fat absorption. Although the change in G/T ratios as a result of taurine supplementation was studied only in two patients, it is reasonable to predict that a change in the conjugation pattern also occured in the others. It has been shown that the effect of taurine feeding, 1.5–4.5 g/day, was fully apparent within 5 days. The amount administered for 6 months in the present study corresponds to a dosage of more than 2 g/day in adults.

As the study was conducted on an ambulatory basis, no attempt was made to monitor dietary intake of fat. It was assumed that variations would be minimized by using each patient as his own control in a cross-over trial. The majority of patients exhibited a decrease in fat loss. Two important observations were made: first, the degree of improvement brought about by taurine was linearly related to the degree of steatorrhea noted on placebo and, second, the fecal loss of the nonpolar, less soluble fatty acids (long-chain saturates) was more extensively reduced. The findings suggest that a shift in the conjugation pattern probably improved the intraluminal phase of fat digestion. At this juncture it is not possible to say whether it is the lipolytic phase, the micellar dispersion step, or both since they are interdependent and closely interrelated. Bile salts are essential in order for pancreatic lipase to absorb to the lipid-water interface of the triglyceride droplet. They have "squatter's rights" and will dislodge other surface active dietary constituents such as proteins and clear the surface for the colipase-lipase complex. Bile acids play a central role for the solubilization of lipolytic products. It has been shown that their physicochemical properties determine their physiological function. Glycine conjugates are capable of dispersing more lipids and have a lower critical micellar concentration than corresponding taurine conjugates. However, these advantages are countered by their tendency to come out of solution in an acidic duodenum and by their greater extent of passive absorption in the jejunum compromising micellar solubilization of lipids distally. The decrease in steatorrhea observed in this study may, therefore, be related to improvement in the formation of micelles which transport products of lipolysis across the unstirred water layer.

Further indication that taurine favorably affected the shuttle of digested fat between the bulk water phase and the absorptive surface is derived from the data on the fecal sequestration of individual fatty acids. The response to taurine affected mainly the long-chain saturates and was inversely proportional to their water solubility values. The differences between palmitic and linoleic acid in terms of absorbability relates to the lesser availability of the former for incorporation into micelles and to its slower uptake by jejunal absorptive cells.

In contrast to other dietary lipids which undergo chemical changes before forming micelles, the bulk (85-90%) of dietary cholesterol and all of biliary cholesterol are unesterified. Free cholesterol requires the presence of bile salts to overcome the resistance of the unstirred water layer. Bile salts vary in their capacity to promote cholesterol absorption. Dihydroxy bile acids are inferior to the trihydroxy forms in this regard and taurine conjugates in vitro are less efficient than glycine conjugates for the solubilization of cholesterol monohydrate. This is perhaps the reason why administration of taurine had no effect on fecal cholesterol excretion. The extent of bile acid loss in the stools did not change with taurine. As bile acid loss reflects their rate of synthesis, these data confirm studies in normal adults and in preterm infants. The absence of alterations in the relative proportion of the two primary bile acids and of their respective degradation products suggest that the predominance of taurine conjugates do not bring about selective changes in the pattern of bile salt synthesis or in their extent of microbial degradation.

As taurine did not affect the excretion of linoleic or of linolenic acid, it is not surprising that the plasma fatty acid patterns did not differ. The relative percentage of total plasma fatty acids accounted by C20:3 ω9 (5-8-11 eicosatrienoic acid) was also unchanged and comparable to other published values in CF on conventional diets. Since it was recently suggested that plasma lipids and lipoproteins are influenced by malabsorption in CF, triglycerides and cholesterol were monitored but no difference was observed during treatment with taurine. Neither in adults nor in preterm infants was taurine shown to modify plasma cholesterol levels.

It has been proposed that taurine plays a role as a modulator of growth. Two species of infant primates (cebus and cynomolgus) were shown to depend on a dietary source of taurine for maximum growth measured by weight gain. However, these observations remain unexplained since dietary intake and absorption were not examined. In preterm infants, taurine had no effect on growth or on fat absorption. The only indication that taurine could directly influence growth in man comes from human lymphoblastoid cells cultured in a taurine-supplemented medium. In the present study, the observation that both mean weight and height velocities, which were below expected values for age during the placebo period, responded to taurine by surpassing expected values is of interest.

Insufficient food intake in the face of increased requirements imposed by infection and chronic lung disease is now considered the more significant cause of malnutrition in CF. A poor response of the lipolytic phase defect to available pancreatic enzyme supplements and concomitant alterations of bile salt metabolism, compromising micellar solubilization of lipolytic products, are also important factors. Claims of added efficacy of a conventional pancreatic enzyme preparation with added bile salts have not been substantiated. Taurine supplementation appears to be promising as an adjuvant form to therapy, particularly in patients with a significant degree of steatorrhea despite adequate pancreatic supplementation.

Following this clinical trial, a further study was carried out to test the effect of taurine on the absorption of a fat meal. In the 4 patients studied following one week on taurine capsules (30 mg/kg/day) or placebo, the postprandial rise in triglycerides, chylomicrons and of the essential fatty acid, linoleic acid, was significantly increased. Of note is the fact that in healthy subject, taurine had no effect.

What is claimed is:

1. An oral composition for alleviating digestive manifestations, in patients afflicted with pancreatic insufficiency, and for enhancing fat absorption in said patients, said compostion comprising therapeutic amounts of taurine and pancrelipase.

2. A method for alleviating digestive manifestations in patients afflicted with pancreatic insufficiency which comprises administering daily to such patients a therapeutic dosage of taurine so as to enhance fat absorption in said patients.

3. A method according to claim 2 wherein the dosage of taurine is about 30 mg/kg of body weight.

4. A method according to claim 2 wherein there is employed a therapeutic amount of mixture of taurine and pancrelipase.

* * * * *